United States Patent [19]

Delavarenne et al.

[11] 4,283,345

[45] Aug. 11, 1981

[54] PROCESS FOR THE PREPARATION OF MONONITRO-1,2,3,4-TETRAHYDROAN-THRAQUINONES

[75] Inventors: Serge Y. Delavarenne, Francheville le Haut; Bernard Dubreux, Francheville le Bas; Pierre Tellier, Sainte Foy les Lyon, all of France

[73] Assignee: Produits Chimiques Ugine Kuhlmann, Courbevoie, France

[21] Appl. No.: 112,001

[22] Filed: Jan. 14, 1980

[30] Foreign Application Priority Data

Jan. 19, 1979 [FR] France .................................. 7901325

[51] Int. Cl.$^3$ .............................................. C07C 50/18
[52] U.S. Cl. ..................................................... 260/369
[58] Field of Search ......................................... 260/369

[56] References Cited

U.S. PATENT DOCUMENTS

| | | | |
|---|---|---|---|
| 2,495,229 | 1/1950 | Pawsey et al. | 260/369 |
| 3,959,318 | 5/1976 | Torisa et al. | 260/369 |

*Primary Examiner*—Patrick Garvin
*Assistant Examiner*—Raymond K. Covington
*Attorney, Agent, or Firm*—Beveridge, DeGrandi, Kline & Lunsford

[57] ABSTRACT

A process is disclosed for the preparation of mononitro derivatives of 1,2,3,4-tetrahydro-anthraquinone from 1,4,4a,9a-tetrahydro-anthraquinone, in which a thermal pretreatment of the 1,4,4a,9a-tetrahydro-anthraquinone is carried out in the presence of a hydrogenation catalyst in an inert atmosphere and in the absence of oxidizing or reducing agents, the anthraquinone by-produced as well as the catalyst are separated and the mixture of 1,2,3,4-tetrahydro-9,10-anthracenediol and 1,2,3,4-tetrahydro-anthraquinone obtained is subjected to a nitration reaction.

27 Claims, No Drawings

PROCESS FOR THE PREPARATION OF MONONITRO-1,2,3,4-TETRAHYDROAN- THRAQUINONES

The present invention relates to a process for the preparation of mononitro derivatives of 1,2,3,4-tetrahydro-anthra quinones from 1,4,4a,9a-tetrahydro-anthraquinone. It is characterized by the fact that it is effected in two successive stages: a pretreatment and a nitration.

It is known from the prior art that the mononitro derivatives of 1,2,3,4-tetrahydro-anthraquinone may be obtained by nitration either of 1,2,3,4-tetrahydro-9,10-anthracenediol, 1,2,3,4,4a,-9a-hexahydro-anthraquinone, or 1,2,3,4-tetrahydro-anthraquinone. These latter compounds are themselves obtained from 1,4,4a,9a-tetrahydro-anthraquinone by a catalytic hydrogenation eventually followed by an isomerization reaction or an oxidation reaction. It has now been found that mononitro-1,2,3,4-tetrahydro-anthraquinones can be obtained starting from 1,4,4a-9a-tetrahydro-anthraquinone provided that the latter is previously subjected to a thermal treatment in an inert atmosphere, in the absence of reducing or oxidizing agents, but in the presence of a hydrogenation catalyst, which leads to a mixture of anthraquinone, 1,2,3,4-tetrahydro-9,10-anthracenediol and 1,2,3,4-tetrahydro-anthraquinone. The anthraquinone is separated and the nitration carried out on the mixture of 1,2,3,4-tetrahydro-9,10-anthracenediol and 1,2,3,4-tetrahydro-anthraquinone leads. This treatment selectively to 5- and 6-mononitro-1,2,3,4-tetrahydro-anthraquinones. The advantage of such a process with respect to the prior art lies essentially in the fact that a catalytic hydrogenation is avoided and possibly also an oxidation reaction, and in consequence complex technologies inherent to reactions effected under pressure is also avoided.

In order to effect the process of the invention the 1,4-4a,9a-tetrahydro-anthraquinone is heated in an inert atmosphere, eventually in a solvent, in the presence of a hydrogenation catalyst. The anthraquinone, the catalyst, and the mixture of 1,2,3,4-tetrahydro-anthraquinone and 1,2,3,4-tetrahydro-9,10-anthracenediol are separated by methods currently used in organic synthesis such as filtration, evaporation, crystallization, etc., and then the nitration reaction is carried out on the mixture of 1,2,3,4-tetrahydro-anthraquinone and 1,2,3,4-tetrahydro-9,10-anthracenediol.

To carry out the pretreatment, monofunctional aliphatic or aromatic alcohols containing from 1 to 10 carbon atoms are preferably selected from among the solvents which can be used. Among the alcohols utilizable according to the invention may be mentioned, for example, methanol, ethanol, propanol and isopropanol, the primary and secondary butanols, tertiobutanol, the amyl alcohols, octanols, benzyl alcohol, etc.

The catalysts utilizable according to the invention are those commonly employed in catalytic hydrogenation reactions, for example, those based on precious metals such as palladium or platinum or those based on nickel such as Raney nickel.

For carrying out the process, solutions of 1,4,4a,9a-tetrahydro-anthraquinone may be used at concentrations varying between 0.5% by weight and saturation at the temperature of the reaction. The latter may be between 20° C. and 160° C., preferably between 70° C. and 120° C. The quantity of catalyst may be between 0.01 and 20% by weight with respect to the quantity of precursor used.

For effecting the nitration of the mixture of 1,2,3,4-tetrahydro-anthraquinone and 1,2,3,4-tetrahydro-9,10-anthracenediol, a mixture of sulfuric and nitric acids may be used or one may operate in pure nitric acid. It is also possible to work in the presence of a solvent on condition that this solvent is inert in the reaction conditions. When operating with a mixture of sulfuric and nitric acids, the concentration of sulfuric acid used is greater than 70%, preferably over 90%. Oleum can also be used instead of sulfuric acid. The concentration of nitric acid then depends on that of the sulfuric acid, but it is preferably greater than 70%. When operating with nitric acid alone, its concentration is at least 90% and preferably at least 98%. The nitration is effected with a molar proportion of nitric acid with respect to the mixture of 1,2,3,4-tetrahydro-9,10-anthracenediol and 1,2,3,4-tetrahydro-anthraquinone at least equal to 1; preferably it is included between 1 and 10. The reaction is carried out at a temperature between 020 and 50° C., preferably between 0° and 30° C.

The following examples illustrate the present invention without limiting it. Examples 1 to 3 relate to the pretreatment of the 1,4,4a,9a-tetrahydro-anthraquinone, while Examples 4 to 6 describe the nitration of the mixture of 1,2,3,4-tetrahydro-anthraquinone and 1,2,3,4-tetrahydro-9,10-anthracenediol.

EXAMPLE 1

5 g of 1,4,4a,9a-tetrahydro-anthraquinone are dissolved in 100 ml of amyl alcohol, and 1 g of palladium at 5% on charcoal is added to this solution. The whole is heated at 120° C. for 5 hours in a stirred reactor maintained under an atmosphere of nitrogen. After cooling, a precipitate is separated which is washed with 100 ml of acetone. Extraction of the precipitate leads to 1 g of anthraquinone. After concentration of the organic phases, 3.8 g of a mixture of 1,2,3,4-tetrahydro-9,10-anthracenediol and 1,2,3,4-tetrahydro-anthraquinone (Mixture A) is obtained.

EXAMPLE 2

The operation is conducted as in Example 1, but is effected at 70° C. instead of 120° C. Starting from 15 g of 1,4,4a,9a-tetrahydro-anthraquinone, 4.5 g of anthraquinone and 10 g of a mixture of 1,2,3,4-tetrahydro-9,10-anthracenediol and 1,2,3,4-tetrahydro-anthraquinone (Mixture B) are obtained.

EXAMPLE 3

20 g of 1,4,4a,9a-tetrahydro-anthraquinone and 2 g of palladium at 5% on charcoal are heated under an atmosphere of nitrogen for one hour at 130° C. After cooling, the solid mixture is washed with 250 ml of acetone. After a similar treatment to that of the preceding Examples 1 and 2, 3.6 g of anthraquinone and 16 g of a mixture of 1,2,3,4-tetrahydro-9,10-anthracenediol and 1,2,3,4-tetrahydro-anthraquinone (Mixture C) are obtained.

EXAMPLES 4, 5 and 6

Into a stirred reactor maintained at 5° C. and containing a mixture of 96% sulfuric acid and 100% nitric acid in a proportion by weight of 5 to 1, is added in a period of 30 minutes an amount of mixture A, B or C of 1,2,3,4-tetrahydro-anthraquinone and 1,2,3,4-tetrahydro-9,10-anthracenediol equal to 1/5 of the weight of the sulfuric-nitric acid solution. The temperature is maintained at between 15° and 18° C. for 3 hours. The precipitate is filtered off, washed with water and dried. The filtrate, diluted with water, gives a second precipitate which is separated, washed with water and dried. The first precipitate is substantially pure 5-nitro-1,2,3,4-tetrahydro-anthraquinone whereas the second precipitate is a mixture of 5-nitro- and 6-nitro-1,2,3,4-tetrahydro-anthraquinone.

The results obtained are shown in Table 1.

TABLE 1

| Example | Mixture/ weight (g) | 5-nitro-1,2,3,4-tetrahydro-anthraquinone | | Mixture of 5-nitro and 6-nitro-1,2,3,4-tetrahydro-anthraquinone (g) |
|---|---|---|---|---|
| | | Weight (g) | Melting point | |
| 4 | A/3.8 | 2.9 | 184° C. | 1.1 |
| 5 | B/10 | 7.8 | 185° C. | 3.0 |
| 6 | C/16 | 12.3 | 184° C. | 4.8 |

What is claimed is:

1. A process for the preparation of mononitro derivatives of 1,2,3,4-tetrahydro-anthraquinones from 1,4,4a,-9a-tetrahydro-anthraquinone which comprises effecting a thermal pretreatment of the 1,4,4a,9a-tetrahydro-anthraquinone in the presence of a hydrogenation catalyst in an inert atmosphere and in the absence of oxidizing or reducing agents which leads to a mixture of anthraquinone, 1,2,3,4-tetrahydro-9,10-anthracenediol and 1,2,3,4-tetrahydro-anthraquinone, separating the anthraquinone by-product and the catalyst and subjecting the mixture of 1,2,3,4-tetrahydro-9,10-anthracenediol and 1,2,3,4-tetrahydro-anthraquinone obtained to a nitration reaction to obtain 5-nitro-1,2,3,4-tetrahydro-anthraquinone and 6-nitro-1,2,3,4-tetrahydro-anthraquinone.

2. A process according to claim 1 in which the pretreatment of the 1,4,4a,9a-tetrahydro-anthraquinone is effected in the presence of a hydrogenation catalyst selected from palladium, platinum or nickel.

3. A process according to claim 2, in which the hydrogenation catalyst used is palladium.

4. A process according to claim 2 or 3 in which the concentration by weight of the hydrogenation catalyst is between 0.01% and 20% by weight of the 1,4,4a,9a-tetrahydro-anthraquinone.

5. The process according to claim 4 in which the pretreatment of the 1,4,4a,9a-tetrahydro-anthraquinone is effected at a temperature between 20° C. and 160° C.

6. The process according to claim 1, 2 or 3 in which the pretreatment of the 1,4,4a,9a-tetrahydro-anthraquinone is effected at a temperature between 20° C. and 160° C.

7. The process according to claim 6 in which the pretreatment of the 1,4,4a,9a-tetrahydro-anthraquinone is effected in the presence of a solvent.

8. The process according to claim 5 in which the pretreatment of the 1,4,4a,9a-tetrahydro-anthraquinone is effected in the presence of a solvent.

9. The process according to claim 4 in which the pretreatment of the 1,4,4a,9a-tetrahydro-anthraquinone is effected in the presence of a solvent.

10. The process according to claim 1, 2 or 3 in which the pretreatment of the 1,4,4a,9a-tetrahydro-anthraquinone is effected in the presence of a solvent.

11. The process according to claim 10 in which the solvent used is a monofunctional aliphatic or aromatic alcohol containing 1 to 10 carbon atoms.

12. The process according to claim 9 in which the solvent used is a monofunctional aliphatic or aromatic alcohol containing 1 to 10 carbon atoms.

13. The process according to claim 8 in which the solvent used is a monofunctional aliphatic or aromatic alcohol containing 1 to 10 carbon atoms.

14. The process according to claim 7 in which the solvent used is a monofunctional aliphatic or aromatic alcohol containing 1 to 10 carbon atoms.

15. The process according to claim 14 in which the concentration by weight of 1,4,4a,9a-tetrahydro-anthraquinone used in the pretreatment thereof is between 0.5% and saturation in the solvent at the reaction temperature.

16. The process according to claim 13 in which the concentration by weight of 1,4,4a,9a-tetrahydro-anthraquinone used in the pretreatment thereof is between 0.5% and saturation in the solvent at the reaction temperature.

17. The process according to claim 12 in which the concentration by weight of 1,4,4a,9a-tetrahydro-anthraquinone used in the pretreatment thereof is between 0.5% and saturation in the solvent at the reaction temperature.

18. The process according to claim 11 in which the concentration by weight of 1,4,4a,9a-tetrahydro-anthraquinone used in the pretreatment thereof is between 0.5% and saturation in the solvent at the reaction temperature.

19. The process according to claim 10 in which the concentration by weight of 1,4,4a,9a-tetrahydro-anthraquinone used in the pretreatment thereof is between 0.5% and saturation in the solvent at the reaction temperature.

20. The process according to claim 9 in which the concentration by weight of 1,4,4a,9a-tetrahydro-anthraquinone used in the pretreatment thereof is between 0.5% and saturation in the solvent at the reaction temperature.

21. The process according to claim 8 in which the concentration by weight of 1,4,4a,9a-tetrahydro-anthraquinone used in the pretreatment thereof is between 0.5% and saturation in the solvent at the reaction temperature.

22. The process according to claim 7 in which the concentration by weight of 1,4,4a,9a-tetrahydro-anthraquinone used in the pretreatment thereof is between 0.5% and saturation in the solvent at the reaction temperature.

23. The process according to claim 1 in which the nitration of the mixture of 1,2,3,4-tetrahydro-9,10-anthracenediol and 1,2,3,4-tetrahydro-anthraquinone is effected in pure nitric acid.

24. The process according to claim 1 in which the nitration of the mixture of 1,2,3,4-tetrahydro-9,10-anthracenediol and 1,2,3,4-tetrahydro-anthraquinone is effected in a mixture of nitric acid and sulfuric acid.

25. The process according to claim 1, 23 or 24 in which the 5-nitro-1,2,3,4-tetrahydro-anthraquinone is selectively separated from the reaction mixture after nitration.

26. The process according to claim 4 in which the pretreatment of the 1,4,4a,9a-tetrahydro-anthraquinone is effected at a temperature between 70° C. and 120° C.

27. The process according to claim 1, 2 or 3 in which the pretreatment of the 1,4,4a,9a-tetrahydro-anthraquinone is effected at a temperature between 70° C. and 120° C.

* * * * *